(12) United States Patent
Stanton et al.

(10) Patent No.: US 8,603,461 B2
(45) Date of Patent: Dec. 10, 2013

(54) PROBIOTIC COMPOSITION SUITABLE FOR ANIMALS

(75) Inventors: Catherine Stanton, Fermoy (IE); Colin Hill, Cork (IE); Ger Fitzgerald, Cork (IE); Paul Ross, Fermoy (IE)

(73) Assignees: TEAGASC—The Agriculture and Food Development Authority, Dublin (IE); University College Cork, Cork (IE)

( * ) Notice: Subject to any disclaimer, the term of this patent is extended or adjusted under 35 U.S.C. 154(b) by 1078 days.

(21) Appl. No.: 11/919,277

(22) PCT Filed: Apr. 6, 2006

(86) PCT No.: PCT/IE2006/000025
§ 371 (c)(1),
(2), (4) Date: Oct. 21, 2009

(87) PCT Pub. No.: WO2006/114778
PCT Pub. Date: Nov. 2, 2006

(65) Prior Publication Data
US 2010/0047209 A1    Feb. 25, 2010

(30) Foreign Application Priority Data
Apr. 26, 2005    (IE) .................................... 2005/0250

(51) Int. Cl.
A23K 3/00      (2006.01)
A23L 1/20      (2006.01)
A01N 63/00     (2006.01)
C12N 1/20      (2006.01)

(52) U.S. Cl.
USPC ............ 424/93.45; 426/53; 426/54; 426/630; 426/807; 435/252.9; 435/822

(58) Field of Classification Search
None
See application file for complete search history.

(56) References Cited

FOREIGN PATENT DOCUMENTS

WO    WO 97/29645 A   *   8/1997
WO    WO 2004/003235 A2 *  1/2004

OTHER PUBLICATIONS

Gardiner et al, "Relative ability of orally adm. *Lactobacillus murinus* to predomonate and persist in the porcies gastroint. tract." Applied and Env. Microbio. vol. 70, No. 4, Apr. 5, 2004, pp. 1895-1906, XP002381023.*

* cited by examiner

*Primary Examiner* — Debbie K Ware
(74) *Attorney, Agent, or Firm* — Jackson Walker L.L.P.

(57) ABSTRACT

The invention provides a probiotic composition to alleviate *Salmonella* infection in farm animals. The composition may comprise at least one of *Lactobacillus murinus*, *Lactobacillus pentosus*, *Lactobacillus salivarius* sub-species *salivarius*, and *Pediococcus pentosaceus*. The composition maybe formulated as an animal feedstuff, or as a pharmaceutical composition.

6 Claims, 3 Drawing Sheets

Fig. 1. Total numbers of rifampicin resistant colonies isolated from faecal samples from pigs administered a probiotic mixture either as fermentate or suspension.

Fig. 2. Numbers of *Salmonella* enumerated by MPN from faeces of pigs challenged with *Salmonella* Typhimurium PT12. Controls: black bars. Suspension: white bars. Fermentate: striped bars. (a). four days post initial infection. (b) eight days p.i. (c). 15 days p.i. (d). 23 days p.i.

(a)

(b)

Fig. 3. Numbers and distribution of individual probiotic cultures isolated from faecal samples from pigs administered a probiotic mixture either as a fermentate or suspension. (a) eight days post initial infection. (b) 23 days p.i.

PROBIOTIC COMPOSITION SUITABLE FOR ANIMALS

This application is a filing under 35 USC 371 of PCT/IE2006/000025, filed Apr. 6, 2006, and further this application claims priority to foreign application number 2005/0520, filed Apr. 26, 2005.

FIELD OF THE INVENTION

The present invention relates to a probiotic composition to alleviate *Salmonella* infection in farm animals. In particular the invention relates to a composition comprising at least one of *Lactobacillus salivarius* subspecies *salivarius* and *Lactobacillus pentosus*. The composition is particularly useful in pig rearing. The invention also relates to an animal feed composition comprising these organisms.

BACKGROUND TO THE INVENTION

Probiotics as applied to humans are defined as live microorganisms which, when administered in adequate numbers, confer a health benefit on the host. The most frequently cited reasons for this probiotic activity include the production of anti-microbial substances such as bacteriocins and lactate and interference with *Salmonella* adhesion to the intestinal wall.

Infection with *Salmonella* results in millions of cases of human foodborne illness every year; the pathogen source varies, but many cases result from the consumption of contaminated porcine meat products (Swanenburg et al., 2001; Anonymous, 2002a). Awareness of food safety issues during all stages of pig meat production is thus vital, particularly with regard to reductions in levels of *Salmonella* contamination. Probiotics, as usually defined, are "live microorganisms which, when administered in adequate amounts, confer a health benefit on the host" (FAO/WHO, 2001). Probiotic properties have been ascribed to many microbial species, but those most commonly used are members of the lactic acid bacteria (LAB) group, particularly *Lactobacillus* and *Bifidobacterium* strains. Several studies have investigated the anti-*Salmonella* effects of potential probiotics using in vitro procedures, particularly growth medium and tissue culture (Drago et al., 1997; Fernandez et al., 2003).

A number of authors have linked the application of LAB probiotics with beneficial effects in models of gastrointestinal infection using small animals. Ogawa et al. (2001) reported that the use of *Lb. casei* Shirota reduced colonization levels and decreased the severity of diarrhoea in *E. coli* O157:H7-infected infant rabbits. Using mice, Johnson-Henry et al. (2004) have noted that a mixture of *Lactobacillus* strains reduces gastric inflammation and bacterial colonization in *Helicobacter pylori*-infected animals. Varied results have been reported with the use of *Salmonella* infection models. Pascual et al. (1999) noted complete exclusion by 21 days of *Salmonella enteritidis* using *Lb. salivarius* in chickens. Recently, La Ragione et al. (2004) observed no beneficial link between pre-treatment with *Lb. johnsonii* and *Salmonella enteritidis* faecal numbers or colonization of the chicken intestine. The same authors did however note that *E. coli* numbers were reduced in the small intestine, but not in the colon, caecum or faeces. They also claimed that the strain was very effective against *Clostridium perfringens*. Silva et al. (2004) observed improved survival for mice pre-treated with *Bif. longum* during *Salmonella* challenge, but no effect on numbers of the pathogen. They postulated that this may be due to a reduced inflammatory response mediated by the probiotic treatment, but not population antagonism.

Many studies investigating the effect of LAB probiotics on gastrointestinal infection in humans concentrate on antagonism of rotavirus infection in infants and *Clostridium difficile* infection in adults. Several reports have claimed beneficial effects for probiotics (particularly *Lb. rhamnosus* GG) in rotaviral infection of children; many of these are reviewed in Alvarez-Olmos and Oberhelman (2001). Among the initial publications in this area was the report by Isolauri et al. (1991) which demonstrated that treatment with *Lb. rhamnosus* GG reduced the duration of rotavirus diarrhoea in children. Reid et al. (2003) have reviewed data claiming a reduction in occurrence of *Clostridium difficile* diarrhoea in humans due to probiotic treatment with *Lb. rhamnosus* GG and *Saccharomyces boulardii*.

With regard to other intestinal disorders, Hilton et al. (1997) claimed that *Lb. rhamnosus* GG decreased the risk of traveller's diarrhoea and Felley et al. (2001) reported that humans fed milk fermented by *Lb. johnsonii* exhibited a significantly reduced density of *H. pylori* and intensity of gastric inflammation. Treatment with a combination of *Lb. acidophilus* and *Bif. infantis* benefited neonates with necrotizing enterocolitis according to Hoyos et al. (1999), who claimed a 60% reduction in mortality due to the treatment.

Reports of the efficacy of probiotic treatment in ameliorating intestinal infection in large animals remain scarce. Zhao et al. (1998) claimed that the application of probiotic *E. coli* (no LAB) reduced the carriage of *E. coli* O157:H7 in cattle. Lema et al. (2001) observed that lambs infected with *E. coli* O157:H7 and then administered *Lb. acidophilus* displayed no beneficial effects. However, feeding the lambs a mixture of *Lb. acidophilus* and *Streptococcus faecium*, or the *Streptococcus* strain alone, significantly lowered numbers of the pathogenic strain. The greatest reduction in numbers was seen with the use of a mixture of *Lb. acidophilus, St. faecium, Lb. casei, Lb. fermentum* and *Lb. plantarum*. Genovese et al. reported in 2000 that an undefined competitive exclusion culture reduced the mortality and shedding of enterotoxigenic *E. coli* in neonatal pigs. The same group (Genovese et al., 2003) also observed that neonatal pigs treated with a similar undefined culture shed significantly lower pathogen numbers after challenge with *Salmonella choleraesuis*, and also exhibited reduced counts in the lower intestine. Whether or not symptoms of infection were alleviated is not described. Fedorka-Cray et al. (1999) reported that the application to *Salmonella choleraesuis*-challenged piglets of a competitive exclusion culture of swine origin led to reduced *Salmonella* counts in their faecal contents and at the ileocolic junction, as well as reduced numbers of *Salmonella* positive gut tissue samples. No clinical symptoms of infection were observed in any animals, including the controls.

Many studies have reported the isolation and selection of probiotic strains for use in pigs (Chang et al, 2001; Gusils et al 2002; Nemcova et al, 1997) but the results of in vivo feeding trials of animals can be variable (Simon et al, 2003). This may in part be explained by the complexity of the intestine, leading to a variation between individual animals. While undefined cultures used in competitive exclusion products can be effective in pigs, uncertainty regarding their exact composition has led to concerns that they may result in pathogen transmission. Therefore there is a need for rational selection characterisation of strains intended for use as probiotic feed additives.

Although pigs harbouring *Salmonella* do not generally display clinical symptoms, carriage of this pathogen in the gastrointestinal tract can leads to carcass contamination at slaughter. This may lead, in turn, to the contamination of porcine meat products. Consumption of pork products containing Salmonella leads to many cases of food borne illness in humans each year. Although certain measures have been shown to reduce the number of cases of human Salmonellosis because of pork. The economic cost associated with Salmonella infections remains high, being estimated at hundreds of millions of dollars annually to the American economy alone.

In this investigation, the pre-treatment of weaned pigs with a defined LAB culture mixture resulting in both reduced numbers of excreted Salmonella as well as an alleviation of clinical symptoms is reported. Molecular analysis of the excreted cultures indicates that the probiotic effects observed may be ascribed to two of the five cultures in the mixture.

OBJECT OF THE INVENTION

One object of the present invention is to provide a composition for the reduction of enteropathogens in farm animals, particularly in pigs. A further object is to reduce carcass contamination with enteropathogens at the time of slaughter in order to reduce pathogen transmission to humans via the food chain. It is a further objection of the invention to provide an alternative to antibiotics in the treatment of carrier animals and also to provide an alternative to the use of antibiotics in animal production, for growth promotion and treatment or prevention of disease in order to reduce the risk of the emergence of antibiotic-resistant pathogens.

When used as microbial feed additives the composition of the invention offers the potential as an alternative to antibiotics, both in controlling pathogen carriage and improving growth rate and feed conversion.

In particular it is an object of the invention to provide a probiotic for use in the pig industry as a means of improving performance and health, particularly because pig rearing has become more intensive in recent years. A still further object is to reduce pathogen carriage in pigs, as pigs are the predominant carriers of Salmonella. Bacterial cultures which have been identified to have inhibitory activity against pathogens must possess certain properties if they are to exert their effect in the small or large intestine. Of prime importance is the ability to overcome to the extremely low pH of gastric acid and the detergent effect of bile salts, and arrive at the site of action in a viable physiological state. If they are to be used as probiotics, cultures must have 'generally regarded as safe' status and also meet a number of technological criteria, e.g. ease of propagation and incorporation into and long term survival in feed products.

SUMMARY OF THE INVENTION

The present invention relates to a probiotic and/or animal feed composition comprising one or more microbial culture of at least one of the group consisting of *Lactobacillus murinus, Lactobacillus pentosus, Lactobacillus salivarius* subspecies *salivarius*, and *Pediococcus pentosaceus*. In favourable embodiments of the invention, the composition comprises a combination of any two or more strains selected from the group consisting of DPC6002, DPC6003, DPC6004, DPC6005 and DPC6006. The cultures have been deposited with the National Collection of Industrial and Marine Bacteria, Aberdeen, Scotland on 25 Apr. 2005 under the Accession Numbers:
NCIMB 41270 *Lactobacillus murinus* DPC 6002
NCIMB 41271 *Lactobacillus murinus* DPC 6003
NCIMB 41272 *Lactobacillus pentosus* DPC 6004
NCIMB 41273 *Lactobacillus salivarius* DPC 6005
NCIMB 41274 *Pediococcus pentosaceous* DPC 6006.

In a particularly preferred embodiment, the composition comprises all five of these strains. The bacterial species or strains are ideally lyophilised or freeze dried where the invention relates to an animal feed composition, the microbial culture may be adapted to provide a total dose of $3 \times 10^{-9}$ colony forming units per day to the animal being fed. In some embodiments, this dose may depend on the weight of the animal.

The invention may also comprise a pharmaceutical composition comprising one or more microbial cultures as described. This may be preferably adapted for suitable administration; for example, in tablet or powder form, potentially with an enteric coating, for oral treatment, or adapted for administration as pessary and so on.

MATERIALS AND METHODS

Bacterial Strains and Culture Conditions

*Lactobacillus murinus* DPC6002 and DPC6003, *Lactobacillus pentosus* DPC6004, *Lactobacillus salivarius* DPC6005 and *Pediococcus pentosaceus* DPC6006, previously isolated from pig faecal contents, were selected from a bank of porcine intestinal isolates on the basis of molecular typing and properties such as antimicrobial activity, bile tolerance and growth in milk (Casey et al., 2004b). The selection of spontaneous rifampicin resistant (Rif$^r$) variants of these porcine isolates to facilitate subsequent enumeration in the pig GIT is described in Gardiner et al. (2004). Both parent and variant strains were routinely cultured at 37° C. in MRS broth (Difco Laboratories, Detroit, Mich., USA) in anaerobic jars with $CO_2$-generating kits (Anaerocult A; Merck, Darmstadt, Germany). *Salmonella typhimurium* PT12 was taken from the collection of the Central Veterinary Research Laboratory (CVRL) and routinely cultured in tryptic soy broth (TSB, Merck, Darmstadt, Germany). This strain is resistant to nalidixic acid, a trait exploited in its faecal enumeration.

Preparation of Probiotic Fermentate and Suspension Treatments

Individual probiotic cultures were grown in milk and mixed to form the fermentate treatment as described previously (Gardiner et al., 2004). For the suspension, 90 ml volumes of MRS broth were inoculated with the appropriate culture at 1% (v/v) and grown overnight in MRS broth at 37° C. Following incubation, the bacteria were harvested by centrifugation, resuspended in 900 ml of 10% RSM and mixed. This suspension was then aliquoted into 100 ml volumes, stored at 4° C. and used within eight days.

Animal Challenge Trial

The pig-feeding trial complied with EU Council Directive 91/630/EEC which lays down minimum standards for the protection of pigs and EU Council Directive 98/58/EC which concerns the protection of animals kept for farming purposes. A total of 15 crossbred (Large White×Landrace) pigs were weaned at 24-28 days and blocked on sex and weight; the animals were then transported from the Moorepark pig production facility to the Central Veterinary Research Laboratory, Abbotstown, Dublin. Pigs within each block were assigned at random to one of three treatment groups (n=5), as follows: (A) control, (B) fermentate and (C) suspension. Each animal was penned individually to prevent cross-contamination. In addition to the cultures or skim milk administered throughout the trial as outlined below, all animals had unrestricted access to water and non-medicated creep feed.

The trial lasted 30 days in total, throughout which time the animals were fed either probiotic culture or skim milk. Pigs receiving probiotic culture were fed 100 ml daily of the appropriate mixture, providing a total dose of either ~$3\times10^{10}$ CFU/day (fermentate) or ~$3\times10^{9}$ CFU/day (suspension). Control animals received 100 ml of skim milk daily. Following 6 days of probiotic administration the animals were challenged orally with $1\times10^{8}$ CFU *S. Typhimurium* daily for three consecutive days. Freshly voided faecal samples were collected from the pigs four days prior to *Salmonella* challenge (day −4) and at 2, 4, 8, 15 and 23 days following first challenge. Probiotic counts were determined at days −4, 2, 8, 15 and 23; *Salmonella* were enumerated at days 4, 8, 15 and 23 post infection.

Microbiological Analysis of Pig Faecal and Cecal Samples

Faecal samples were stored at 4° C. and analysed within 24 h of collection; samples were homogenised in maximum recovery diluent (D, Lab M, UK) as 10-fold dilutions using a stomacher (Lab-Blender 400; Seward Medical, London, UK), further diluted in MRD and appropriate dilutions pourplated. The administered strains were enumerated following anaerobic incubation for five days at 37° C. on *Lactobacillus* selective agar with rifampicin, i.e. LBS agar (Becton Dickinson, Cockeysville, Md., USA) containing 150 μg/ml of rifampicin as a selective agent and 50 U/ml nystatin (Sigma) to inhibit yeasts and moulds. In addition, up to twenty colonies randomly selected from LBS-RIF plates from each animal at day 8 and day 23 p.i. were cultured in MRS broth and analysed by RAPD PCR as outlined below.

Preliminary experiments suggested that the numbers of *Salmonella* recovered from the pig faeces would be very low and not suitable for counting by direct plating. Faecal *Salmonella* numbers were therefore enumerated by three tube most probable number (MPN) method. 10 g of faeces were added to 90 ml of buffered peptone water (BPW, Lab M) and homogenized for four minutes. The homogenate was then divided into three 50 ml, three 5 ml, and three 0.5 ml aliquots; the 0.5 ml aliquots were further diluted by the addition of 1 ml BPW. The tubes were incubated overnight at 37° C., following which 0.1 ml from each tube was added to 9.9 ml of Rappaport-Vassiliadis broth (RV, Lab M) and incubated for 18-24 h at 42° C. Isolation was performed on brilliant green agar (BG, Lab M) containing 100 μg/ml each of nalidixic acid and novobiocin (Sigma). The number of *Salmonella* present in each sample was calculated using the MPN table of de Man (1983).

Genetic Fingerprinting by RAPD PCR

Samples from probiotic-fed animals were plated on media selective for the remarked probiotic cultures, and up to 20 of the resultant colonies from each of the five animals per group were selected and incubated in MRS medium. Genomic DNA was isolated from 1.5 ml of the overnight cultures according to the method outlined by Coakley et al. (1996). The extracted DNA was then used as a template in PCR amplifications, which were performed using the random primer R2 (5' GTGATGTGCTGGTGTTATGTTTA 3'; MWG Biotech, Ebersberg, Germany) as previously outlined (Gardiner et al., 1998), with the following modifications; PCR amplifications were performed in a total volume of 50 μl in an Eppendorf DNA thermal cycler (Eppendorf Scientific Inc., Westbury, N.Y.) with 1.25 U of Taq DNA polymerase (Bioline, London, UK) added to the reaction mix. The PCR products (10 μl of each reaction) were analyzed on a 1.5% (wt/vol) agarose (Sigma) gel, using a 100 bp ladder (New England Biolabs, Hitchin, Hertfordshire, UK) as a molecular weight standard. The banding patterns obtained from faecal isolates were compared with those of control DNA from each of the cultures present in the probiotic mixture, allowing for the identification of individual porcine cultures in each faecal sample.

Physical Indicators of Illness

Pigs were weighed initially in Moorepark before their transport to Abbotstown and again at the end of the feeding period prior to their slaughter. Their weights and percentage increases were determined individually and collectively, with comparisons being made between the control and probiotic treatments.

Faecal samples collected from the pen of each animal between three and seven days post infection were examined and the presence or absence of scour noted.

Observations of the severity of diarrhoea and the attitude of the animals were combined to form a clinical scoring system (detailed in Table 3). These scores were recorded daily for the first nine days post infection and indicate the severity of illness associated with each animal over this period Statistical Analysis Data pertaining to animal weight, temperature, presence or absence of scour, or clinical score were studied in one of two ways. For investigation of data regarding individual probiotic groups, one way analysis of variance (ANOVA) was used to analyse normally distributed data. Data exhibiting a non-normal pattern of distribution was analysed by the non-parametric Kruskal-Wallis one-way ANOVA on ranks test, with post-hoc comparison by Dunnett's method. Where data was considered on the basis of a single probiotic grouping (i.e. suspension and fermentate combined), Student's t-test was used for data satisfying assumptions of normality; where non-parametric analysis was required, the Mann-Whitney U-test was used. *Salmonella typhimurium* counts were transformed to log base n before statistical analysis. These data were then analysed by ANOVA, with post-hoc multiple comparison procedures performed using the Holm-Sidak method. To account for the small sample sizes, the Kolmogorov-Smirnov test was performed using a P value cut off of 0.01. Differences were considered significant if $P<0.05$.

EXAMPLES

Pig Weights

The weights of the animals in the control group increased by a mean of 246% during the period under investigation, while those animals whose diet incorporated probiotic treatment (combined probiotic suspension and fermentate treatments) exhibited a significantly greater ($p<0.05$) weight increase over the trial period. Individually, lower mean weight increases were seen for both the suspension and fermentate, although these differences were not significant at $p<0.05$. No significant differences were observed between the weights of the pigs fed either of the probiotic treatments (Table 1).

Diarrhoea

Among animals fed control milk, thirteen individual samples (of 25 total) were positive for the presence of diarrhoea (Table 2). This compared with only six positive samples (of 50 overall) collected from animals fed probiotic; three each from animals fed the probiotic as suspension and fermentate (Table 2). Statistical analysis indicated that the feeding of probiotic to animals was associated with a significantly lower risk of diarrhoea. Of the five pigs in the control grouping, four exhibited diarrhoea during the five-day period. Of the animals fed probiotic, two of those fed the probiotic suspension gave scour positive stool samples, with only one fermentate-fed animal giving positive stools.

Clinical Scores

Statistical analysis of the mean score of animals in the control grouping (7.0) and animals fed probiotic when taken as a single group (suspension and fermentate scores combined) (2.1), resulted in a significantly lower score for the probiotic fed animals. When the probiotic treatments were compared separately (suspension v control; fermentate v control) against the control group, their mean clinical scores, while lower, were not significantly so (Table 3).

Faecal Excretion of Administered Cultures

Figure 1:
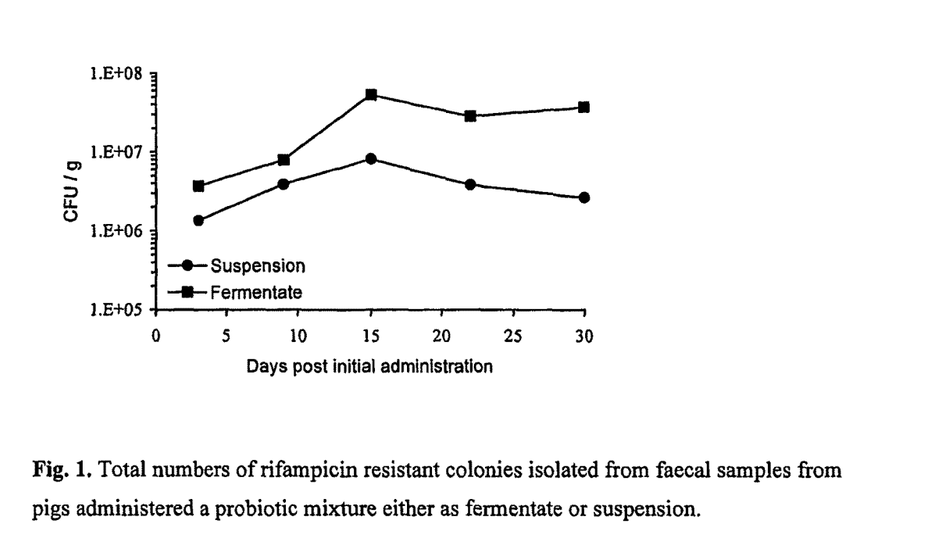
FIG. 1 shows total numbers of rifampicin resistant colonies isolated from faecal samples from pigs administered a probiotic mixture either as fermentate or suspension.

Total numbers of excreted probiotic cultures rose in all treated animals to a peak of between $7 \times 10^6$ and $5 \times 10^7$ CFU/g at 15 days after first administration (eight days post infection). Compared to suspension-treated animals, higher total counts were observed in all cases from pigs fed the fermentate (FIG. 1); this is in keeping with the higher initial inoculum numbers of the fermentate mixture.

Anti-*Salmonella* Effects

Figure 2:
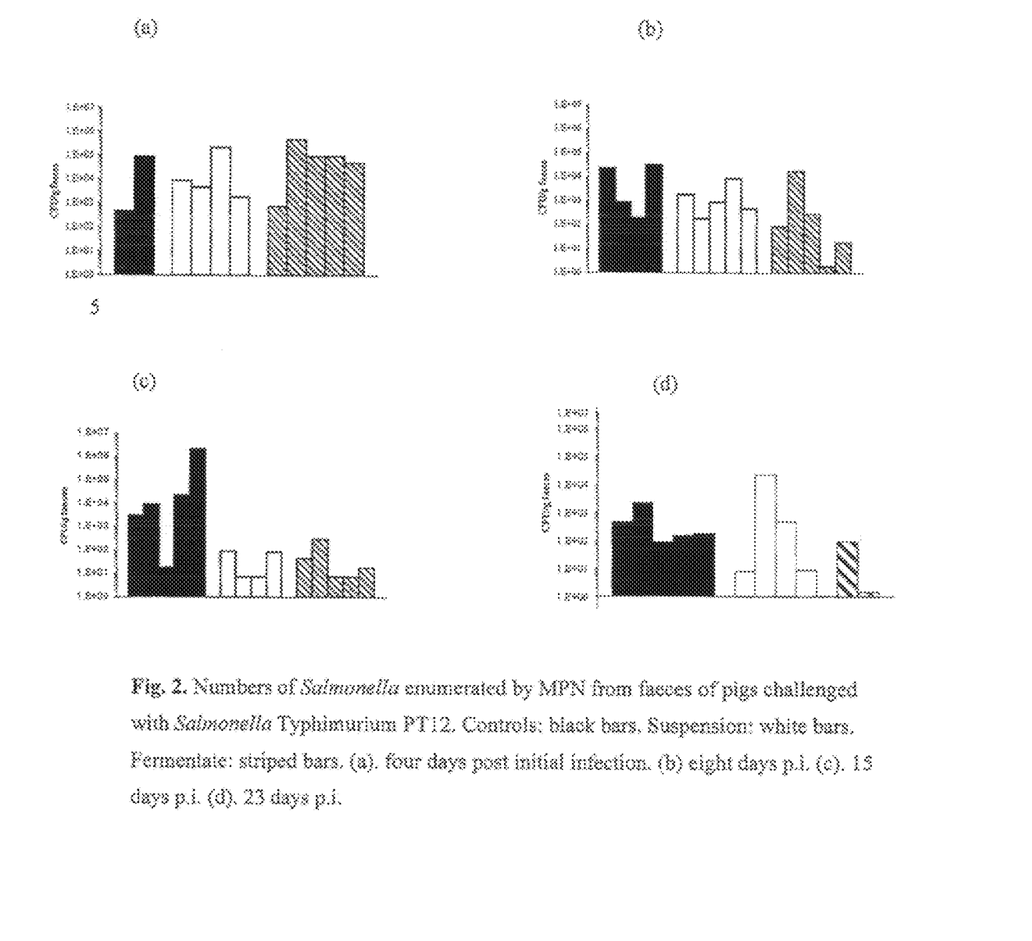
FIG. 2 shows numbers of *salmonella* enumerated by MPN from faeces of pigs challenged with *salmonella* Typhimurium PT 12: (a) four days post initial infection, (b) eight days p.i., (c) 15 days p.i., and (d) 23 days p.i. Controls are represented by black bars. Suspension is represented by white bars. Fermentate is represented by striped bars.

*Salmonella* numbers (cfu/g) in faecal samples of control and treatment groups were enumerated by the MPN technique at regular intervals post infection. No statistical differences were observed between control and probiotic treatment groups at four days post infection (FIG. 2). At eight days post infection, the mean *Salmonella* numbers of the suspension and fermentate groups ($2.53 \times 10^3$ and $3.8 \times 10^3$ cfu/g faeces, respectively) were lower that of the control sample ($1.33 \times 10^4$ cfu/g), although this difference was not shown to be statistically significant. At 15 days post infection, the numbers of *Salmonella* detected in the control samples were significantly higher than those of the probiotic grouping; analysed individually, the mean values of the suspension and fermentate treatment groups (48 and 76 cfu/g faeces, respectively) were also shown to be statistically significantly different from that of the control ($4.47 \times 10^5$ cfu/g) (FIG. 2). Analysis of the final faecal samples from the animals, taken 23 days after the initial *Salmonella* infection, indicated no significant difference in numbers of *Salmonella* between the control and probiotic groupings, although numbers were very low in all cases (FIG. 2).

RAPD Analysis of Excreted Cultures

Figure 3:
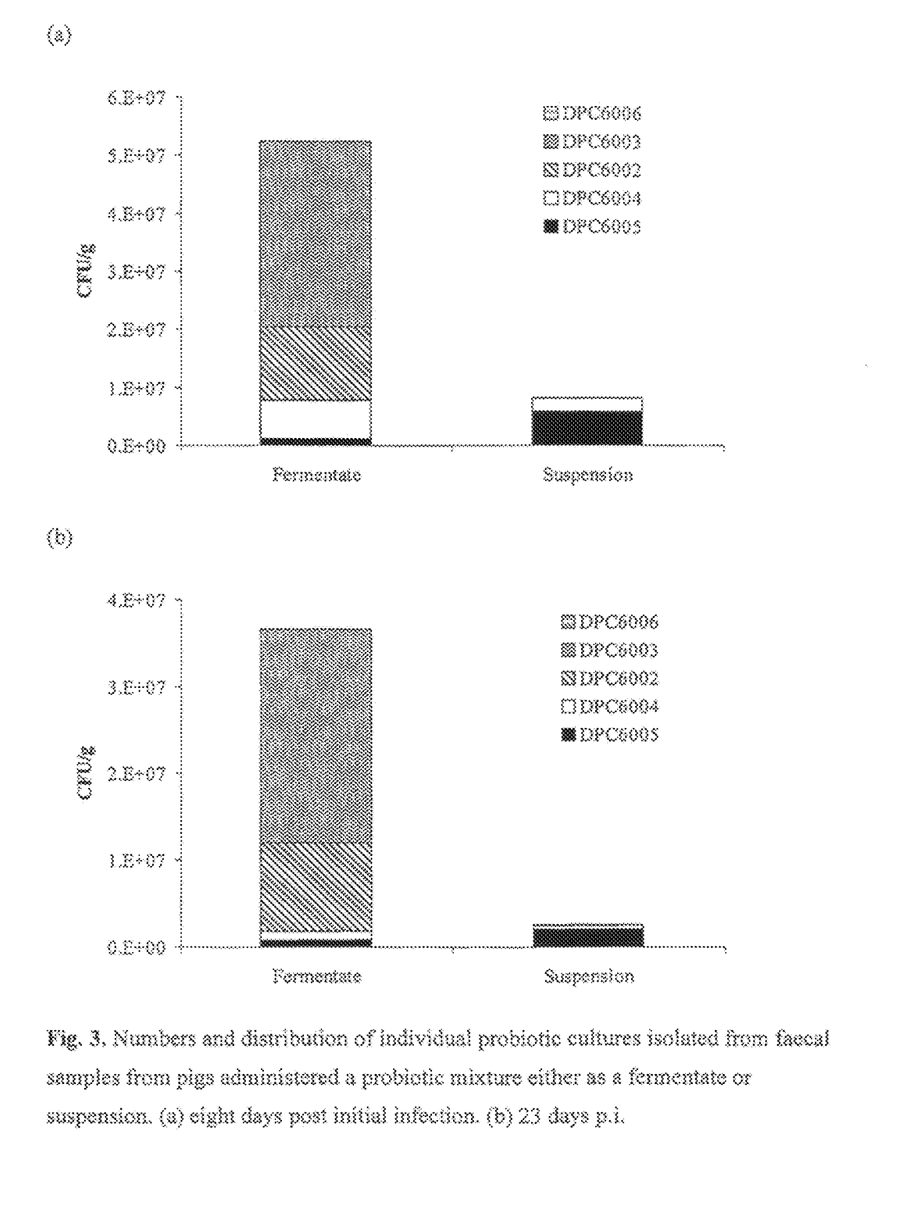
FIG. 3 shows numbers and distribution of individual probiotic cultures isolated from faecal samples from pigs administered a probiotic mixture either as a fermentate or suspension: (a) eight days post initial infection, and (b) 23 days p.i.

Faecal samples taken at days eight and 23 post infection from animals fed probiotic as suspension or fermentate were analysed by RAPD PCR and the distribution of the individual porcine cultures within the mixture identified. (FIG. 3).

At eight and 23 days post infection, *Lb. murinus* 46 (DPC 6003) was by far the most prevalent culture recovered from animals receiving the fermentate treatment, accounting for 60% of colonies analysed at day 8 and 67% at day 23. Relatively large numbers of *Lb. murinus* DPC 6002 were also recovered, accounting for 24% of colonies at day 8 and approx 28% at day 23. At eight days post infection, 12.5% of colonies taken from fermentate samples were identified as *Lb. pentosus* DPC 6004, while this culture only accounted for 3% of colonies from the same animals at day 23 post infection. Two percent of colonies taken from fermentate samples at both eight and 23 days post infection were identified as *Lb. salivarius* DPC 6005. Only 1 colony of *Pediococcus pentosaceus* DPC 6006 was recovered at day 8 pi, while not accounting for any of the isolates at day 23 (FIG. 3).

The proportions of colonies recovered from faecal samples of animals administered the suspension treatment varied considerably from those observed in fermentate fed animals. *Lb. salivarius* DPC 6005 accounted for 72% and 77% of colonies recovered at day 8 and day 23 pi, respectively. The remaining 28% of colonies at day 8 were all identified as *Lb. pentosus* DPC 6004; this probiotic represented 19% of the total at day 23. Low numbers of both *Lb. Murinus* DPC 6002 (2.5%) and *Lb. murinus* DPC 6003 (1%) were also identified at day 23. No colonies of *P. pentosaceus* DPC 6006 were identified in either case (FIG. 3).

When the overall numbers of Rif'-resistant probiotic colonies were enumerated, it was observed that total numbers recovered from fermentate samples were several orders of magnitude higher than those from suspension samples; this is in keeping with the higher initial numbers in the fermentate feed. Numbers at day 23 were slightly lower than those at day 8. Analysis of the total numbers of individual probiotic cultures at these time points yielded an interesting result. While large numbers of *Lb. murinus* strains DPC 6002 and 6003 were naturally recovered from fermentate samples but not from suspension samples, the combined numbers (cfu/g) of DPC 6005 and DPC 6004 were very similar in both the fermentate and suspension samples at both day 8 ($8.0 \times 10^6$ cfu/g and $8.08 \times 10^6$ cfu/g, respectively) and day 23 ($1.9 \times 10^6$ cfu/g and $1.0 \times 10^6$ cfu/g, respectively) (FIG. 3).

Discussion

*Salmonella* infection remains a major cause of foodborne gastroenteritis, with an estimated 160,000 cases of human salmonellosis reported annually in the European Union, at an economic cost of up to €2.8 billion (Anonymous, 2002a; Anonymous, 2002b). *S. typhimurium* and *S. enteritidis* are the most common causes of human illness (Anonymous, 2002a). In the United States, the FoodNet programme has noted that the estimated incidence of *Salmonella* infection did not change significantly in the years 1996 to 2002, in contrast to several other major foodborne disease agents (Anonymous, 2003). Carriage by pigs of *Salmonella* in the gastrointestinal tract (GIT) can lead to carcass contamination at slaughter which may lead, in turn, to the contamination of porcine meat products. Such contamination was recently demonstrated by a survey showing that up to 6% of retail pork sausages in Ireland tested positive for *Salmonella* (Boughton et al., 2004). Consumption of pork products containing *Salmonella* leads to many cases of foodborne illness each year (Swanenburg et al., 2001; Anonymous, 2003); *S. typhimurium* remains the serovar most commonly isolated from pigs in Ireland and elsewhere (Davies et al., 2000; Quirke et al., 2001, Casey et al., 2004a).

The selection from the pig intestine and characterisation of the probiotic bacteria used in this study has previously been described (Casey et al., 2004b). The ability of the five strains to survive transit through the pig GIT in non-infected animals has also been examined (Gardiner et al., 2004). The present invention examined the efficacy of the five strains in improving the outcome of *Salmonella* infection in weaned pigs.

A combination of any two of the strains, in any suitable ratio, is conceived for some embodiments; and further embodiments may comprise combinations, in any suitable ratio, of three or four of the species. Furthermore, in one favourable embodiment, the invention comprises a combination of all five strains: DPC6002, DPC6003, DPC6004, DPC6005 and DPC6006.

In the described examples, the administration of either form of probiotic mixtures of the invention clearly led to amelioration of physical symptoms in the animals, although not always significantly so. In all cases, no significant differences were seen between results for the fermentate and suspension groupings. Perhaps the most obvious symptom of gastrointestinal infection is the presence of diarrhoea (scour). While over 50% of stool samples from control animals were scour positive, the corresponding figure for probiotic treated pigs was significantly lower at 12% in both cases. The development of scour by pigs in production facilities is normally treated with antibiotics; lower incidences of scour may lead to improved food quality through reduced antibiotic use. Ogawa et al. (2001) have demonstrated a reduced severity of diarrhoea in *E. coli* O157:H7 infected rabbits; we are not aware of any reports of probiotic-mediated reduction in incidence of diarrhoea in any model of *Salmonella* infection to date.

A clinical scoring system was devised to indicate the severity of illness in each animal, with higher scores indicating more severe illness. While both probiotic treatment groups of the examples yielded lower mean scores than the control grouping, these were not significantly lower. However, investigation of the culture-fed animals as a single group (based on results detailed below) did lead to significantly lower clinical scores. Lower scores signal an overall 'less sick' animal. It is perhaps worth noting that the veterinarian responsible for animal welfare during the trial observed what she termed a "massive difference" between control and treatment animals. As well as the use of antibiotics mentioned above, a 'happy' animal requires less attention from its owner as well as reduced veterinary intervention, resulting in a lowered financial burden on the owner.

The physical attribute of perhaps most importance to pig producers is the rate of weight gain of the animals. As with the clinical scores detailed above, the weight gain across the trial period of the animals in the individual probiotic groups, while greater than that of control animals, was not quite significantly so using $P<0.05$. Classification of probiotic-treated animals as one group did, again, result in significantly higher weight gain. This is likely to be of particular significance to pig producers, as heavier animals attract a price premium. While improved growth performance in pigs due to the administration of probiotics has previous been demonstrated (Chang et al., 2001), there has been, to our knowledge, no examination of the effects of probiotics on weight gain in pigs during gastrointestinal infection.

While the results already detailed are perhaps of greatest importance to producers of pigs, the effects of probiotic treatment on the level of *Salmonella* carriage is of most significance to consumers. Application of either of the probiotic treatments in this study resulted in an improvement in the numbers of faecal *Salmonella*, which has positive potential for the safety of porcine food products. While lower mean counts were observed for probiotic-treated animals at a number of sampling points, these differences were significant at 15 days post infection, with the control animals exhibiting a mean *Salmonella* count approximately 10,000-fold higher than either of the probiotic groups. Due to the speculative nature of the dilutions used for the MPN technique, counts were not obtained for some samples; this made comparison at day 4 p.i. difficult as only two counts were obtained for control animals. While not willing to be bound by theory, the lack of observed probiotic effect at this point may be due to high numbers of *Salmonella* 'flushing through' shortly after inoculation. *Salmonella* counts rose sharply for control animals at 15 days p.i. and pigs in the suspension group at 23 days p.i. One possibility is that this may be due to reinfection of animals from their surroundings. Such environmental infection has been shown to be an important factor in *Salmonella* carriage in pigs (Hurd et al., 2001; Gebreyes et al., 2004). A number of reports have been published describing probiotic-mediated reduction in intestinal *Salmonella* numbers (Fedorka-Cray et al., 1999; Genovese et al., 2003); these studies have, however, utilised the scholeraesuis serovar, which has not been implicated as a major source of human disease. Both of these groups use undefined competitive exclusion cultures; it is possible that the unknown composition of cultures of this type may lead to pathogen transmission. These studies have also used neonatal pigs who have not yet established a stable gut flora, in contrast to our use of older, weaned animals.

RAPD PCR analysis of excreted probiotic cultures showed the two *Lb. murinus* strains dominating in animals administered the probiotic fermentate. This is in keeping with our previous study (Gardiner et al., 2004), during which animals were also fed probiotic-fermented milk. However, examination of colonies isolated from animals treated with the same strains in the form of a milk suspension demonstrated that the two *Lb. murinus* strains comprised only a small proportion of excreted probiotics. An examination of the composition of the milk fermentate showed the cultures present in approximately the same proportions at which they were inoculated (data not shown); it is thus likely that the milk fermentation process gives the *Lb. murinus* strains a selective advantage in subsequent intestinal conditions. Investigation of the numbers of excreted individual cultures (FIG. 3) revealed similar combined levels of *Lb. pentosus* DPC6004 and *Lb. salivarius* subsp. *salivarius* DPC 6005 in both fermentate- and suspension-fed animals at day 8 p.i. and day 23 p.i. Due to the lack of differences observed in the results for both probiotic groupings, it is our belief that any probiotic effect can be ascribed to the 'common factor' in the two treatments, i.e. *Lb. pentosus* DPC6004 and *Lb. salivarius* subsp. *salivarius* DPC 6005. This is supported by our earlier results (Gardiner et al., 2004) showing no decrease in numbers of *Enterobacteriaceae* isolated from the faeces of pigs fed either of the *Lb. murinus* strains, but large reductions in animals fed any of strains DPC6004, DPC6005 or DPC6006 or a mixture of all five strains. It is also obvious that the predominant strains returned from animals administered probiotic mixtures may not be the actual cause of any observed positive effects. We have also noted, however, that *Lb. salivarius* subsp. *salivarius* DPC6005 produces a bacteriocin active against *Lb. delbruekii* subsp. *bulgaricus* (data not shown). The observation of a similar 'active ingredient' in both probiotic groups tested led us to combine the data from both groups in some statistical tests, as described earlier.

The data presented here shows that the probiotic mixtures of the invention lead to an amelioration of clinical symptoms in *S. typhimurium*-infected pigs early in the course of infection, and reduced pathogen counts over a longer timeframe. The probiotics examined are thus of interest to both those involved in the pig production industry and those with an interest in food safety. The results obtained also demonstrate the validity of the in vitro and in vivo procedures used to isolate and select the bacteria (Casey et al., 2004b; Gardiner et al., 2004). The similarities between the pig and human gastrointestinal tracts suggest that the probiotics examined in this study may also have potential in cases of human salmonellosis. This marks, to our knowledge, the fast example of a defined probiotic treatment having beneficial effects on both the clinical and microbiological symptoms of pigs challenged with *S. typhimurium*.

In conclusion, weaned pigs were administered a mixture of five probiotic strains either as a milk fermentate or milk suspension and the effects on subsequent *Salmonella typh-*

*imurium* infection investigated. The probiotic mixture consisted of two strains of *Lactobacillus murinus* and one strain each of *Lb. salivarius* subsp. *salivarius, Lb. pentosus* and *Pediococcus pentosaceous*. Animals treated with probiotic exhibited reduced morbidity and a decreased incidence of diarrhoea. These animals also gained weight at a greater rate than control pigs administered skim milk. Mean faecal numbers of *Salmonella* were significantly reduced in probiotic-treated animals at 15 days post infection. RAPD PCR analysis of excreted probiotic cultures suggested that the probiotic effects observed may be ascribed to two of the five strains, *Lb. salivarius* subsp. *salivarius* and *Lb. pentosus*. These strains in particular offer significant potential for use in the pig production industry.

REFERENCES

Alvarez-Olmos, M. I. and Oberhelman, R. A. 2001. Probiotic agents and infectious diseases: a modern perspective on a traditional therapy. Clin Infect Dis. 32(11):1567-76.

Anonymous. 2002a. Trends and sources of zoonotic agents in animals, feeding stuffs, food and man in the European Union and Norway in 2000. Available at http://europa.eu.int/comm/food/fs/sfp/mr/mr08_en.pdf.

Anonymous. 2002b. Directive of the European Parliament and of the Council on the monitoring of zoonoses and zoonotic agents, amending Council Decision 90/424/EEC and repealing Council Directive 92/117/EEC. Available at http://europa.eu.int/eur-lex/pri/en/lip/latest/doc/2002/com2002_0684en01.doc.

Anonymous. 2003. Preliminary FoodNet Data on the Incidence of Foodborne Illnesses—Selected Sites, United States, 2002. Morbidity and Mortality Weekly Report 52: 340-3.

Boughton, C., Leonard, F. C., Egan, J., Kelly, G., O'Mahony, P., Markey, B. K. and Griffin, M. 2004. Prevalence and number of *Salmonella* in Irish retail pork sausages. J. Food Protect. 67: 1834-39.

Casey, P. G., Butler, D., Gardiner, G. E., Tangney, M., Simpson, P., Lawlor, P. G., Stanton, C., Ross, R. P., Hill, C. and Fitzgerald, G. F. 2004a. *Salmonella* carriage in an Irish pig herd: correlation between serological and bacteriological detection methods. J. Food Protect. 67(12): 2797-800.

Casey, P. G., Casey, G. D., Gardiner, G. E., Tangney, M., Stanton, C., Ross, R. P., Hill, C. and Fitzgerald, G. F. 2004b. Isolation and characterization of anti-*Salmonella* lactic acid bacteria from the porcine gastrointestinal tract. Lett. Appl. Microbiol. 39(5): 431-8.

Chang, Y. H., J. K. Kim, H. J. Kim, W. Y. Kim, Y. B. Kim, and Y. H. Park. 2001. Selection of a potential probiotic *Lactobacillus* strain and subsequent in vivo studies. Antonie Van Leeuwenhoek 80:193-9.

Coakley, M., R. P. Ross, and D. Donnelly. 1996. Application of the polymerase chain reaction to the rapid analysis of brewery yeast strains. J. Inst. Brew. 102: 349-354.

Davies, R., G. Paiba, S. Evans, and B. Dalziel. 2000. Surveys for *Salmonella* in pigs, cattle and sheep at slaughter in Great Britain. Vet. Rec. 147: 695.

Drago, L., Gismondo, M. R., Lombardi, A., de Haen, C. and Gozzini, L. 1997. Inhibition of in vitro growth of enteropathogens by new *Lactobacillus* isolates of human intestinal origin. FEMS Microbiology Letters 153: 455-463.

FAO/WHO. 2001. Health and nutritional properties of probiotics in food including powder milk with live lactic acid bacteria—joint FAO/WHO expert consultation. Cordoba, Argentina, 1-4 Oct. 2001. http://www.who.int/foodsafety/publications/fs_management/probiotics/en/

Fedorka-Cray, P. J., Bailey, J. S., Stern, N. J., Cox, N. A., Ladely, S. R. and Musgrove, M. 1999. Mucosal competitive exclusion to reduce *Salmonella* in swine. J Food Prot. 62(12):1376-80.

Felley, C. P., Corthesy-Theulaz, I., Rivero, J. L., Sipponen, P., Kaufmann, M., Bauerfeind, P., Wiesel, P. H., Brassart, D., Pfeifer, A., Blum, A. L. and Michetti, P. 2001. Favourable effect of an acidified milk (LC-1) on *Helicobacter pylori* gastritis in man. Eur J Gastroenterol Hepatol. 13(1): 25-9.

Fernandez, M. F., Boris, S. and Barbes, C. 2003. Probiotic properties of human lactobacilli strains to be used in the gastrointestinal tract. Journal of Applied Microbiology 94: 449-455.

Gardiner, G., Ross, R. P., Collins, J. K., Fitzgerald, G. and Stanton, C. 1998. Development of a probiotic cheddar cheese containing human-derived *Lactobacillus paracasei* strains. Appl. Environ. Microbiol. 64: 2192-9.

Gardiner, G. E., Casey, P. G., Casey, G., Lynch, P. B., Lawlor, P. G., Hill, C., Fitzgerald, G. F., Stanton, C. and Ross, R. P. 2004. Relative ability of orally administered *Lactobacillus murinus* to predominate and persist in the porcine gastrointestinal tract. Appl Environ Microbiol. 70(4): 1895-906.

Gebreyes, W. A., P. R. Davies, P.-K. Turkson, W. E. Morgan Morrow, J. A. Funk and C. Altier. 2004. *Salmonella enterica* serovars from pigs on farms and after slaughter and validity of using bacteriologic data to define herd *Salmonella* status. J. Food Protect. 67: 691-697.

Genovese, K. J., Anderson, R. C., Harvey, R. B., Callaway, T. R., Poole, T. L., Edrington, T. S., Fedorka-Cray, P. J. and Nisbet, D. J. 2003. Competitive exclusion of *Salmonella* from the gut of neonatal and weaned pigs. J Food Prot. 66(8):1353-9.

Genovese, K. J., Anderson, R. C., Harvey, R. B. and Nisbet, D. J. 2000. Competitive exclusion treatment reduces the mortality and faecal shedding associated with enterotoxigenic *Escherichia coli* infection in nursery-raised neonatal pigs. Can. J. Vet. Res. 64: 204-7.

Hilton, E., Kolakowski, P., Singer, C. and Smith, M. 1997. Efficacy of *Lactobacillus* GG as a Diarrheal Preventive in Travelers. J Travel Med. 4(1):41-43.

Hoyos, A. B. 1999. Reduced incidence of necrotizing enterocolitis associated with enteral administration of *Lactobacillus acidophilus* and *Bifidobacterium infantis* to neonates in an intensive care unit. Int J Infect Dis. 3(4):197-202.

Hurd, H. S., J. K. Gailey, J. D. McKean and M. H. Rostagno. 2001. Rapid infection in market-weight swine following exposure to a *Salmonella typhimurium*-contaminated environment. Am. J. Vet. Res. 62: 1194-1197.

Isolauri, E., Juntunen, M., Rautanen, T., Sillanaukee, P. and Koivula, T. 1991. A human *Lactobacillus* strain (*Lactobacillus casei* sp strain GG) promotes recovery from acute diarrhoea in children. Paediatrics. 88(1):90-7.

Johnson-Henry, K. C., Mitchell, D. J., Avitzur, Y., Galindo-Mata, E., Jones, N. L. and Sherman, P. M. 2004. Probiotics reduce bacterial colonization and gastric inflammation in *H. pylori*-infected mice. Dig. Dis. Sci. 49: 1095-102.

La Ragione, R. M., Narbad, A., Gasson, M. J. and Woodward, M. J. 2004. In vivo characterization of *Lactobacillus johnsonii* FI9785 for use as a defined competitive exclusion agent against bacterial pathogens in poultry. Lett Appl Microbiol. 38(3):197-205.

Lema, M., Williams, L. and Rao, D. R. 2001. Reduction of faecal shedding of enterohemorrhagic *Escherichia coli* O157:H7 in lambs by feeding microbial feed supplement. Small Rumin. Res. 39(1):31-39.

de Man, J. C. (1983). MPN tables, corrected. Eur J Appl Microbiol 17: 301-5.

Ogawa, M., Shimizu, K., Nomoto, K., Takahashi, M., Watanuki, M., Tanaka, R., Tanaka, T., Hamabata, T., Yamasaki, S, and Takeda, Y. 2001. Protective effect of *Lactobacillus casei* strain Shirota on Shiga toxin-producing *Escherichia coli* O157:H7 infection in infant rabbits. Infect. Immun. 69: 1101-8.

Pascual, M., Hugas, M., Badiola, J. I., Monfort, J. M. and Garriga, M. 1999. *Lactobacillus salivarius* CTC2197 prevents *Salmonella enteritidis* colonization in chickens. Appl Environ Microbiol. 65(11):4981-6.

Quirke, A.-M., N. Leonard, G. Kelly, J. Egan, P. B. Lynch, T. Rowe and P. J. Quinn. 2001. Prevalence of *Salmonella* serotypes on pig carcasses from high- and low-risk herds slaughtered in three abattoirs. Berl. Munch. Tierarztl. 114: 360-2.

Reid, G., Jass, J., Sebulsky, M. T. and McCormick, J. K. 2003. Potential uses of probiotics in clinical practice. Clin. Microbiol. Rev. 16: 658-72.

Silva, A. M., Barbosa, F. H., Duarte, R., Vieira, L. Q., Arantes, R. M. and Nicoli, J. R. 2004. Effect of *Bifidobacterium longum* ingestion on experimental salmonellosis in mice. J Appl Microbiol. 97(1):29-37.

Swanenburg, M., H. A. Urlings, J. M. Snijders, D. A. Keuzenkamp and F. van Knapen. 2001. *Salmonella* in slaughter pigs: prevalence, serotypes and critical control points during slaughter in two slaughterhouses. Int. J. Food Microbiol. 70: 243-254.

Zhao, T., Doyle, M. P., Harmon, B. G., Brown, C. A., Mueller, P. O. and Parks, A. H. 1998. Reduction of carriage of enterohemorrhagic *Escherichia coli* O157:H7 in cattle by inoculation with probiotic bacteria. J Clin Microbiol. 36(3):641-7.

TABLE 1

Percentage increase in weight of pigs across 30-day trial period.

| | % increase in weight | | |
|---|---|---|---|
| Pig no. | Control | Fermentate | Suspension |
| 1 | 227 | 318 | 317 |
| 2 | 254 | 316 | 253 |
| 3 | 271 | 250 | 272 |
| 4 | 272 | 256 | 268 |
| 5 | 205 | 287 | 379 |
| Mean | 246 | 285 | 298 |

Animals were weighed prior to initial culture administration and subsequent to final treatment.

TABLE 2

Presence or absence of diarrhoea in faecal samples of *Salmonella Typhimurium*-infected pigs at the indicated number of days post initial infection.

| Pig | Day 3 | Day 4 | Day 5 | Day 6 | Day 7 |
|---|---|---|---|---|---|
| (a) | | | | | |
| 1 | Y | Y | Y | Y | Y |
| 2 | Y | Y | Y | Y | N |
| 3 | N | N | N | N | N |
| 4 | N | Y | Y | Y | N |
| 5 | N | N | Y | Y | Y |
| (b) | | | | | |
| 1 | N | N | N | N | N |
| 2 | N | N | N | N | N |
| 3 | Y | N | N | N | N |
| 4 | Y | Y | N | N | N |
| 5 | N | N | N | N | N |
| (c) | | | | | |
| 1 | N | N | N | N | N |
| 2 | Y | Y | Y | N | N |
| 3 | N | N | N | N | N |
| 4 | N | N | N | N | N |
| 5 | N | N | N | N | N |

Y = diarrhoea positive; N = diarrhoea negative.
(a) control animals.
(b) animals administered probiotic fermentate.
(c) animals administered probiotic suspension.

TABLE 3

Clinical score for pigs included in the different treatment groups for the first nine days post infection.

| | Total clinical score | | |
|---|---|---|---|
| Pig no. | Control | Fermentate | Suspension |
| 1 | 15 | 1 | 2 |
| 2 | 7 | 7 | 2 |
| 3 | 0 | 0 | 3 |
| 4 | 4 | 0 | 6 |
| 5 | 9 | 0 | 2 |
| Mean | 7.0 | 1.6 | 3.0 |

Scoring system: Attitude: 0 = normal; 1 = must be stimulated to get up; 2 = gets up with help; 3 = cannot get up. Faeces: 0 = normal. 1 = soft. 2 = mild diarrhoea. 3 = severe, watery diarrhoea.

The invention claimed is:

1. A probiotic composition comprising one or more biologically pure microbial cultures selected from the group consisting of *Lactobacillus murinus, Lactobacillus pentosus, Lactobacillus salivarius* sub-species *salivarius*, and *Pediococcus pentosaceous*, for use in the reduction or control of *Salmonella* carriage, wherein the biologically pure cultures are selected from the group consisting of the cultures deposited with the National Collection of Industrial and Marine Bacteria, Aberdeen, Scotland on 25 Apr. 2005 under the Accession Numbers:
NCIMB 41270 *Lactobacillus murinus* DPC 6002
NCIMB 41271 *Lactobacillus murinus* DPC 6003
NCIMB 41272 *Lactobacillus pentosus* DPC 6004
NCIMB 41273 *Lactobacillus salivarius* DPC 6005 and
NCIMB 41274 *Pediococcus pentosaceous* DPC 6006.

2. A probiotic composition comprising all of the strains as claimed in claim 1.

3. A probiotic composition as claimed in any preceding claim wherein the microbial cultures is lyophilised or freeze dried.

4. A probiotic composition as claimed in claim 1, formulated for use as an animal feed for use in the reduction or control of *Salmonella* carriage.

5. A probiotic composition as claimed in claim 2, formulated for use as an animal feed for use in the reduction or control of *Salmonella* carriage.

6. A probiotic composition as claimed in claim 3, formulated for use as an animal feed for use in the reduction or control of *Salmonella* carriage.

* * * * *